US008834526B2

(12) United States Patent
Garcia (10) Patent No.: US 8,834,526 B2
(45) Date of Patent: Sep. 16, 2014

(54) METHODS AND APPARATUS FOR TREATING SPINAL STENOSIS

(76) Inventor: Rolando Garcia, Golden Beach, FL (US)

( * ) Notice: Subject to any disclaimer, the term of this patent is extended or adjusted under 35 U.S.C. 154(b) by 1067 days.

(21) Appl. No.: 11/891,582

(22) Filed: Aug. 9, 2007
(Under 37 CFR 1.47)

(65) Prior Publication Data
US 2009/0018658 A1    Jan. 15, 2009

Related U.S. Application Data

(60) Provisional application No. 60/836,783, filed on Aug. 9, 2006.

(51) Int. Cl.
*A61B 17/70*    (2006.01)
*A61B 17/064*    (2006.01)
*A61B 17/80*    (2006.01)

(52) U.S. Cl.
CPC ......... *A61B 17/7062* (2013.01); *A61B 17/7059* (2013.01); *A61B 17/0642* (2013.01); *A61B 17/8085* (2013.01)
USPC .......................... 606/248; 606/249; 623/17.11

(58) Field of Classification Search
USPC ...................... 606/246–248; 623/17.11–17.16
See application file for complete search history.

(56) References Cited

U.S. PATENT DOCUMENTS

| | | |
|---|---|---|
| 2,677,369 A | 5/1954 | Knowles |
| 3,426,364 A | 2/1969 | Lumb |
| 3,648,691 A | 3/1972 | Lumb |
| 3,875,595 A | 4/1975 | Froning |
| 4,369,769 A | 1/1983 | Edwards |
| 4,554,914 A | 11/1985 | Kapp |
| 4,570,618 A | 2/1986 | Wu |
| 4,599,086 A | 7/1986 | Doty |
| 4,604,995 A | 8/1986 | Stephens |
| 4,611,582 A | 9/1986 | Duff |
| 4,643,178 A | 2/1987 | Nastari |
| 4,685,447 A | 8/1987 | Iversen |
| 4,696,290 A | 9/1987 | Steffee |
| 4,728,329 A | 3/1988 | Mansat |
| 4,795,466 A | 1/1989 | Stuhmer |
| 4,805,602 A | 2/1989 | Puno |
| 4,913,134 A | 4/1990 | Luque |
| 4,917,700 A | 4/1990 | Aikins |
| 4,946,378 A | 8/1990 | Hirayama |
| 4,969,888 A | 11/1990 | Scholten et al. |
| 5,011,484 A | 4/1991 | Breard |
| 5,030,220 A | 7/1991 | Howland |
| 5,035,716 A | 7/1991 | Downey |
| 5,047,055 A | 9/1991 | Bao |
| 5,059,194 A | 10/1991 | Michelson |
| 5,084,049 A | 1/1992 | Asher |
| 5,092,866 A | 3/1992 | Breard |
| 5,092,893 A | 3/1992 | Smith |
| 5,123,926 A | 6/1992 | Pisharodi |
| 5,167,662 A | 12/1992 | Hayes |
| 5,180,381 A | 1/1993 | Aust |
| 5,180,393 A | 1/1993 | Commarmond |
| 5,192,327 A | 3/1993 | Brantigan |
| 5,282,863 A | 2/1994 | Burton |
| 5,290,312 A | 3/1994 | Kojimoto |

(Continued)

*Primary Examiner* — Pedro Philogene
*Assistant Examiner* — Christina Negrellirodrigue
(74) *Attorney, Agent, or Firm* — Jonathan Spangler; Jennifer Russell (57) ABSTRACT

This invention relates generally to spine surgery and, in particular, to methods and apparatus for treating spinal stenosis.

29 Claims, 8 Drawing Sheets

(56) References Cited

U.S. PATENT DOCUMENTS

| | | |
|---|---|---|
| 5,304,178 A | 4/1994 | Stahurski |
| 5,306,309 A | 4/1994 | Wagner |
| 5,352,225 A | 10/1994 | Yuan |
| 5,375,823 A | 12/1994 | Navas |
| 5,387,213 A | 2/1995 | Breard |
| 5,390,683 A | 2/1995 | Pisharodi |
| 5,395,372 A | 3/1995 | holt |
| 5,415,661 A | 5/1995 | Holmes |
| 5,443,514 A | 8/1995 | Steffee |
| 5,458,638 A | 10/1995 | Kuslich |
| 5,458,641 A | 10/1995 | Ramirez |
| 5,458,643 A | 10/1995 | Oka |
| 5,470,333 A | 11/1995 | Ray |
| 5,480,401 A | 1/1996 | Navas |
| 5,496,318 A | 3/1996 | Howland |
| 5,505,732 A | 4/1996 | Michelson |
| 5,514,180 A | 5/1996 | Heggeness |
| 5,534,028 A | 7/1996 | Bao |
| 5,534,029 A | 7/1996 | Shima |
| 5,540,688 A | 7/1996 | Navas |
| 5,540,689 A | 7/1996 | Sanders |
| 5,549,679 A | 8/1996 | Kuslich |
| 5,562,736 A | 10/1996 | Ray |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi |
| 5,658,286 A | 8/1997 | Save |
| 5,672,175 A | 9/1997 | Martin |
| 5,674,295 A | 10/1997 | Ray |
| 5,674,296 A | 10/1997 | Bryan |
| 5,676,702 A | 10/1997 | Ratron |
| 5,702,455 A | 12/1997 | Saggar |
| 5,725,582 A | 3/1998 | Bevan |
| 5,766,252 A | 6/1998 | Henry |
| 5,814,046 A | 9/1998 | Hopf |
| 5,824,098 A | 10/1998 | Stein |
| 5,836,948 A * | 11/1998 | Zucherman et al. .......... 606/249 |
| 5,860,977 A | 1/1999 | Zucherman |
| 5,865,846 A | 2/1999 | Bryan |
| 5,876,404 A | 3/1999 | Zucherman |
| 5,885,299 A | 3/1999 | Winslow |
| 5,888,224 A | 3/1999 | Beckers |
| 5,888,226 A | 3/1999 | Rogozinski |
| 5,904,686 A | 5/1999 | Zucherman |
| 5,976,186 A | 11/1999 | Bao |
| 6,001,130 A | 12/1999 | Bryan |
| 6,022,376 A | 2/2000 | Assell |
| 6,048,342 A | 4/2000 | Zucherman |
| 6,068,630 A | 5/2000 | Zucherman |
| 6,074,390 A | 6/2000 | Zucherman |
| 6,090,112 A | 7/2000 | Zucherman |
| 6,113,639 A | 9/2000 | Ray |
| 6,149,652 A | 11/2000 | Zucherman |
| 6,156,038 A | 12/2000 | Zucherman |
| 6,156,067 A | 12/2000 | Bryan |
| 6,183,471 B1 | 2/2001 | Zucherman |
| 6,190,387 B1 | 2/2001 | Zucherman |
| 6,234,705 B1 | 5/2001 | Troxell |
| 6,235,030 B1 | 5/2001 | Zucherman |
| 6,238,397 B1 | 5/2001 | Zucherman |
| 6,280,444 B1 | 8/2001 | Zucherman |
| 6,290,700 B1 | 9/2001 | Schmotzer |
| 6,332,882 B1 | 12/2001 | Zucherman |
| 6,332,883 B1 | 12/2001 | Zucherman |
| 6,355,038 B1 | 3/2002 | Pisharodi |
| 6,379,355 B1 | 4/2002 | Zucherman |
| 6,402,750 B1 | 6/2002 | Atkinson |
| 6,419,676 B1 | 7/2002 | Zucherman |
| 6,419,677 B2 | 7/2002 | Zucherman |
| 6,451,019 B1 | 9/2002 | Zucherman |
| 6,451,020 B1 | 9/2002 | Zucherman |
| 6,478,796 B2 | 11/2002 | Zucherman |
| 6,500,178 B2 | 12/2002 | Zucherman |
| 6,514,255 B1 | 2/2003 | Ferree |
| 6,514,256 B2 | 2/2003 | Zucherman |
| 6,558,387 B2 | 5/2003 | Errico |
| 6,626,944 B1 | 9/2003 | Taylor |
| 6,652,527 B2 | 11/2003 | Zucherman |
| 6,652,534 B2 | 11/2003 | Zucherman |
| 6,669,697 B1 | 12/2003 | Pisharodi |
| 6,695,842 B2 | 2/2004 | Zucherman |
| 6,695,882 B2 | 2/2004 | Bianchi |
| 6,699,246 B2 | 3/2004 | Zucherman |
| 6,699,247 B2 | 3/2004 | Zucherman |
| 6,712,819 B2 | 3/2004 | Zucherman |
| 6,723,097 B2 | 4/2004 | Fraser |
| 6,740,090 B1 | 5/2004 | Cragg |
| 6,761,720 B1 * | 7/2004 | Senegas .................. 606/249 |
| 6,796,983 B1 | 9/2004 | Zucherman |
| 7,172,593 B2 * | 2/2007 | Trieu et al. .................. 606/281 |
| 7,201,775 B2 * | 4/2007 | Gorensek et al. ........... 623/17.11 |
| 7,238,204 B2 * | 7/2007 | Le Couedic et al. ....... 623/17.11 |
| 7,273,498 B2 | 9/2007 | Bianchi |
| 7,824,433 B2 * | 11/2010 | Williams .................. 606/285 |
| 2001/0020188 A1 | 9/2001 | Sander |
| 2001/0021850 A1 | 9/2001 | Zucherman |
| 2003/0040746 A1* | 2/2003 | Mitchell et al. .................. 606/61 |
| 2003/0045935 A1 | 3/2003 | Angelucci |
| 2003/0060823 A1 | 3/2003 | Bryan |
| 2004/0106995 A1* | 6/2004 | Le Couedic et al. ....... 623/17.11 |
| 2005/0165398 A1 | 7/2005 | Reiley |
| 2006/0085070 A1 | 4/2006 | Kim |
| 2006/0241601 A1* | 10/2006 | Trautwein et al. ............... 606/61 |
| 2006/0293662 A1* | 12/2006 | Boyer et al. .................... 606/61 |
| 2007/0032790 A1 | 2/2007 | Aschmann |
| 2007/0043361 A1 | 2/2007 | Malandain |
| 2007/0073292 A1 | 3/2007 | Kohm |
| 2008/0015701 A1 | 1/2008 | Garcia |
| 2008/0319549 A1 | 12/2008 | Greenhalgh |

* cited by examiner

METHODS AND APPARATUS FOR TREATING SPINAL STENOSIS

CROSS REFERENCES TO RELATED APPLICATIONS

The present application is a nonprovisional patent application claiming benefit under 35 U.S.C. §119(e) from U.S. Provisional Application Ser. No. 60/836,783, filed on Aug. 9, 2006, the entire contents of which are hereby expressly incorporated by reference into this disclosure as if set forth fully herein.

BACKGROUND OF THE INVENTION

I. Field of the Invention

This invention relates generally to spine surgery and, in particular, to a method and apparatus for installing a surgical implant to treating spinal stenosis.

II. Discussion of the Prior Art

Spinal stenosis is a degenerative narrowing of the spinal canal, nerve root canals and/or intervertebral foramina caused by bone and/or ligament hypertrophy in local, segmental or generalized regions. The narrowing results in compression of spinal nerves and nerve roots, causing a constellation of symptoms, including neck or lower back pain, neurogenic claudication, and extremity pain. Spinal stenosis can occur at any region of the spine, but occurs most frequently in the lumbar region. The leading cause of spinal stenosis is normal wear and tear on the spine, occurring in virtually the entire adult population during the natural process of aging, although spinal stenosis can occur at any age due to trauma, disease, or some medical conditions.

The most common indication for surgery in persons aged over 60 in the United States is lumbar spinal stenosis. Surgery is currently the only treatment designed and proven to provide long term relief from lumbar spinal stenosis. Decompressive laminectomy is the most common surgery performed in order to correct lumbar spinal stenosis. The goal of this operation is to create more room for the nerve root that has been encroached upon by the facet joints of the vertebra.

Decompressive laminectomy and other types of surgery to treat spinal stenosis are considered relatively invasive surgical procedures, especially when accompanied by a fusion. Increasingly, surgeons are looking for improved methods of effecting less invasive treatments for spinal stenosis with greater efficiency. The present invention is directed at overcoming, or at least improving upon, the disadvantages of the prior art.

SUMMARY OF THE INVENTION

The present invention is directed at a surgical method and apparatus for treating spinal stenosis without the need for a laminectomy. The invention includes an apparatus configured for placement between two spinous processes and adapted to fuse to one spinous process. The device permits spinal flexion, movement bending the spine forward, while limiting spinal extension, movement bending the spine backward. The invention may be used in the cervical, thoracic, or lumbar spine.

Various mechanisms may be used to enhance fusion, or bony re-growth, between the implant and the spinous process, including the implant shape, porosity, anchors, and the inclusion of bone-growth promoting substances. Fusion may be augmented by including any number of suitable fusion-inducing materials within the implant, including but not limited to BMP1, 2, 3, 4, 5, 6, 7, 8, 9, 10, 11, 12, 13, 14 . . . n, demineralized bone matrix, allograft cancellous bone, autograft bone, hydroxy appetite, coral and/or other highly porous substance.

The spacer may be constructed of bone or non-bone material. The bone embodiment involves manufacturing the spacer from a suitable allograft bone, including but not limited to clavicle, rib, humerus, radius, ulna, metacarpal, phalanx, femur, tibia, fibula, or metatarsal bone. The non-bone embodiment involves manufacturing the spacer from suitable non-bone materials, including but not limited to polyaryletherketone (PEEK) and polyaryletherketoneketone (PEKK).

The SPS assembly includes a spacer and two flanges. At least one flange includes a fixation aperture and a flange fixation element. The spacer includes a main chamber and a fusion notch. The fusion notch is defined as the space between the two flanges.

In one embodiment the spacer is designed to fuse to only the first spinous process, resulting in what is called "hemifusion". This may be accomplished by securing the flange fixation element through one face of the flange aperture, into the first spinous process, and through the opposite face of the flange aperture. The flange fixation element may consist of any sort of screw, pin, nail, tack, staple, etc, and serves to mechanically affix the spacer to the spinous process. The flange fixation element may be crafted from any number of materials, including but not limited to titanium, stainless steel, or any other suitable metal or non-metal.

Although illustrated with regard to the superior spinous process, it will be appreciated that the spacer may also be coupled to only the inferior spinous process without departing from the scope of the present invention. The spacer, once positioned, serves to distract the interspinous process space, which advantageously restores foraminal height in stenotic patients and may also indirectly decompress the intervertebral space.

A main chamber extends through the lateral sides of the spacer. The main chamber may be provided in any of a variety of suitable shapes in addition to the generally cylindrical shape as shown, including but not limited to a generally oblong, triangular, rectangular shape and/or combinations thereof. The flanges have a flange aperture that extends through each face of the flange. A pair of insertion tool apertures may be located on either the posterior or anterior side of the spacer and extend a portion of the way through the spacer. The fusion notch includes a slot or indent to receive a portion of the first spinous process (or other vertebral structure) to enhance fusion. The fusion notch may be located generally towards the middle portion of the top of the spacer. The notch helps center the spacer relative to the first spinous process. This accommodating shape provides stability and increased fusion due to the relatively generous amount of spacer surface area in contact with the spinous process.

According to one embodiment of the present invention, the spacer may be provided with a second notch opposite the fusion notch, giving the spacer a modified "H" shape. The second notch is capable of resting on the adjacent spinous process during use, which may assist in maintaining the spacer in a desired position relative to the adjacent spinous process. In one embodiment, the spacer is generally U-shaped, however, alternate embodiments of the device could utilize any number of different shapes, including, by way of example only, an "H" shape, or a wedged or "V" shape.

In one embodiment the fusion notch may be further provided with slots extending into the main chamber. When the spacer is coupled to the spinous process, these slots will establish direct communication between fusion-inducing compounds provided within the main chamber and the lower aspect of the spinous process, which advantageously augments the ability of the spacer to fuse to the spinous process (particularly if the spacer is constructed of non-bone materials).

During insertion of the spinous process spacer of the present invention, it may become necessary to sever the supraspinous and interspinous ligaments. In one embodiment of the present invention the SPS assembly may further include an overlay designed to extend between the first and second spinous processes in order to restore the integrity and functional benefits of the supraspinous ligament. By way of example only, overlay may be any material suitable for restoring the structural and functional integrity of the supraspinous ligament, including but not limited to a surgical mesh or patch manufactured from any suitable biocompatible fiber or textile (such as polyester) via any suitable technique (such as embroidery).

Anchors may be used to secure the overlay to the spinous processes. Preferably, anchors are inserted into the posterior portion of the spinous process, however it is contemplated that anchors may be inserted into any portion of the spinous process suitable to provide purchase. Optionally, side anchors may be inserted into the side of the spinous processes to further secure the overlay to the bone. Anchors and side anchors may be any device suitable for attaching the overlay to the bone, including but not limited to pins, screws, nails, tacks, staples, and the like.

The SPS assembly may further include an overlay designed to extend between the first and second spinous processes in order to restore the integrity and functional benefits of the supraspinous ligament and the intraspinous ligament. Anchors may be used to secure the overlay to the spinous processes. Preferably, anchors are inserted into the posterior portion of the spinous process, however it is contemplated that anchors may be inserted into any portion of the spinous process suitable to provide purchase. Optionally, side anchors may be inserted into the sides of the spinous processes to further secure the overlay to the bone. Anchors and side anchors may be any device suitable for attaching the overlay to the bone, including but not limited to pins, screws, nails, tacks, staples, and the like.

Although shown as separate components, it is contemplated that overlays may be integrally formed with spacer such that the overlay and spacer are inserted contemporaneously.

The SPS assembly of the present invention may be introduced into a spinal target site through the use of any of a variety of suitable instruments having the capability to releasably engage the spacer.

BRIEF DESCRIPTION OF THE DRAWINGS

The invention will be more fully understood from the following detailed descriptions taken in conjunction with the accompanying drawings, in which.

DESCRIPTION OF THE PREFERRED EMBODIMENT

Illustrative embodiments of the invention are described below for the purposes of understanding the principles of the invention. No limitation of the scope of the invention is therefore intended. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The methods and apparatus for treating spinal stenosis disclosed herein boasts a variety of inventive features and components that warrant patent protection, both individually and in combination.

Figure 1:
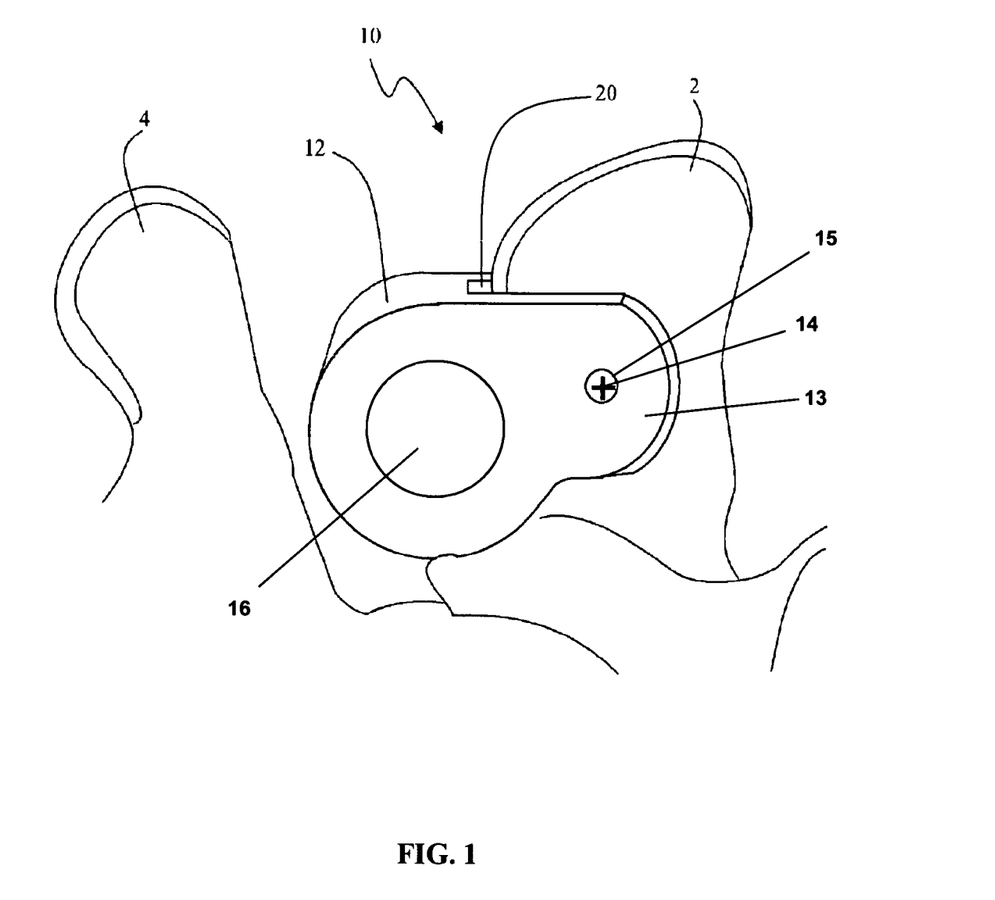
FIG. 1 is a side view of a spinous process spacer implanted between the spinous processes of a pair of adjacent vertebrae, according to one embodiment of the present invention, illustrating the spinous process spacer affixed to one spinous process.

FIG. 1 is a side view of one example of a spinous process spacer ("SPS") 10 of the present invention inserted between the spinous processes 2, 4 of a pair of adjacent vertebrae. The SPS 10 includes a body 12 and two flanges 13. In the example shown in FIG. 1, the two flanges 13 engage either side of the first spinous process 2. Each flange 13 includes an aperture 14 dimensioned to receive at least a portion of a fixation element 15. The body 12 includes a main chamber 16 and a fusion notch 20.

The SPS 10 may be of bone or non-bone construction. The bone embodiment involves manufacturing the SPS 10 from a suitable allograft bone, including but not limited to clavicle, rib, humerus, radius, ulna, metacarpal, phalanx, femur, tibia, fibula, or metatarsal bone. The non-bone embodiment involves manufacturing the SPS 10 from suitable non-bone materials, including but not limited to polyaryletherketone (PEEK) and polyaryletherketoneketone (PEKK).

As shown by way of example in FIG. 1, in one embodiment the SPS 10 is designed to fuse to only the first spinous process 2, resulting in what is called "hemi-fusion". This may be accomplished, by way of example only, by securing the fixation element 15 such that it passes through the aperture 14 on one flange 13, into and through the first spinous process 2, and at least partially into the corresponding aperture 14 on a second flange 13 on the opposite side of the first spinous process 2, best shown in FIG. 3. The fixation element 15 may consist of any sort of screw, pin, nail, tack, staple, etc, and serves to mechanically affix the SPS 10 to the spinous process 2. The fixation element 15 may be crafted from any number of materials, including but not limited to titanium, stainless steel, or any other suitable metal or non-metal.

Although illustrated with regard to the superior spinous process 2, it will be appreciated that the SPS 10 may also be coupled to only the inferior spinous process 4 without departing from the scope of the present invention. The SPS 10, once positioned, serves to distract the interspinous process space, which advantageously restores foraminal height in stenotic patients and may also indirectly decompress the intervertebral space.

Figure 2:
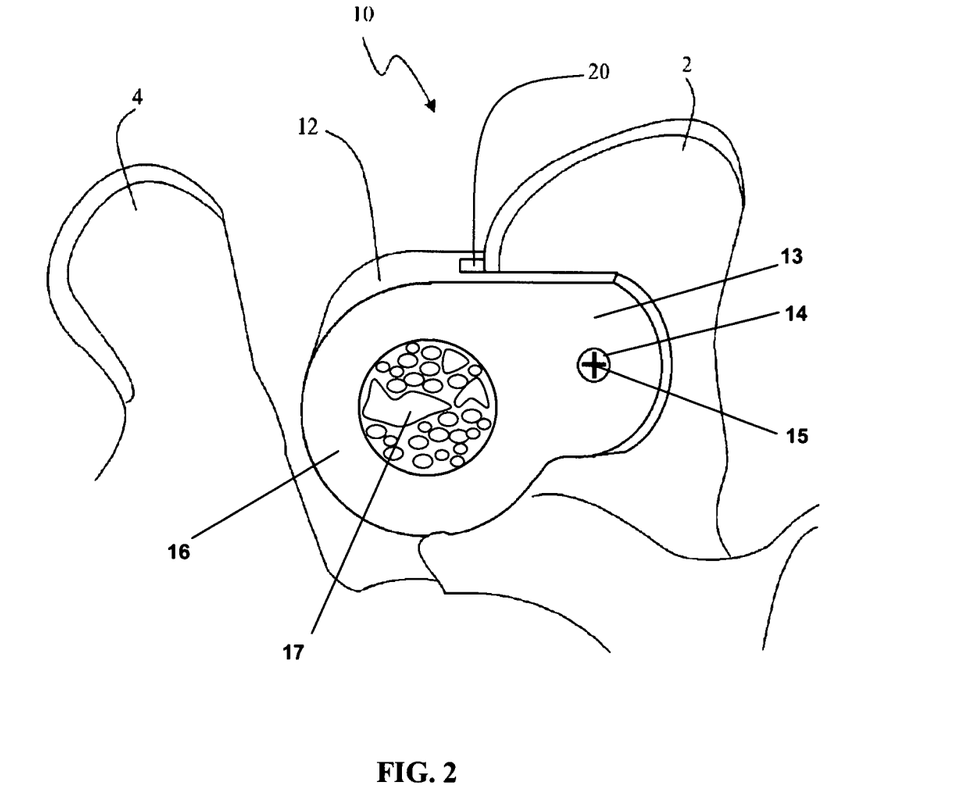
FIG. 2 is a side view of the spinal process spacer assembly of FIG. 1 including bone growth promoting material.

As shown in FIG. 2, fusion may be augmented by including any number of suitable fusion-inducing materials 17 within the main chamber 16, including but not limited to BMP1, 2, 3, 4, 5, 6, 7, 8, 9, 10, 11, 12, 13, 14 . . . n, demineralized bone matrix, allograft cancellous bone, autograft bone, hydroxy appetite, coral and/or other highly porous substance.

Figure 3:
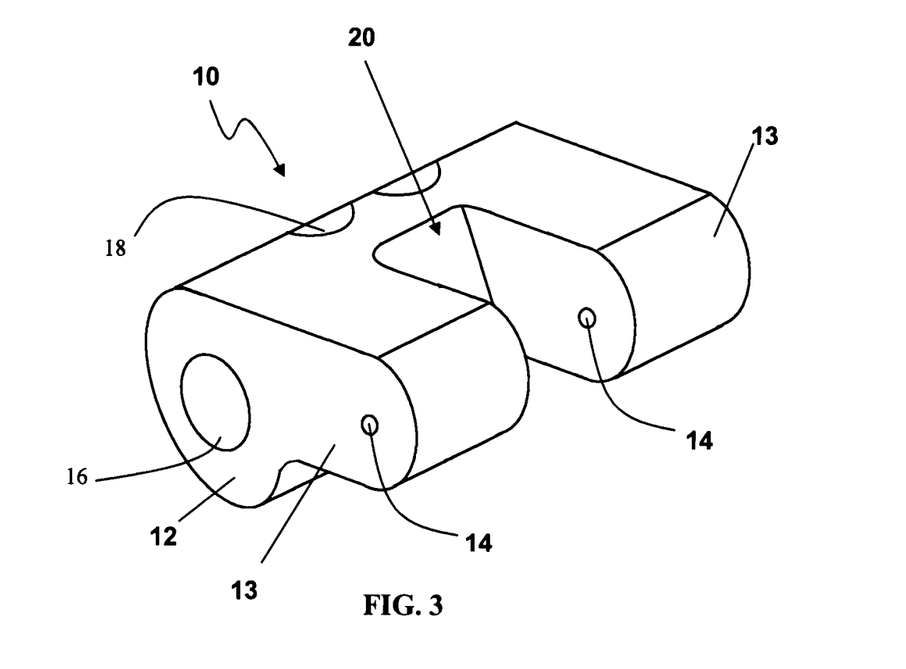
FIG. 3 is a perspective view of a spinous process spacer according to one embodiment of the present invention.
Figure 4:
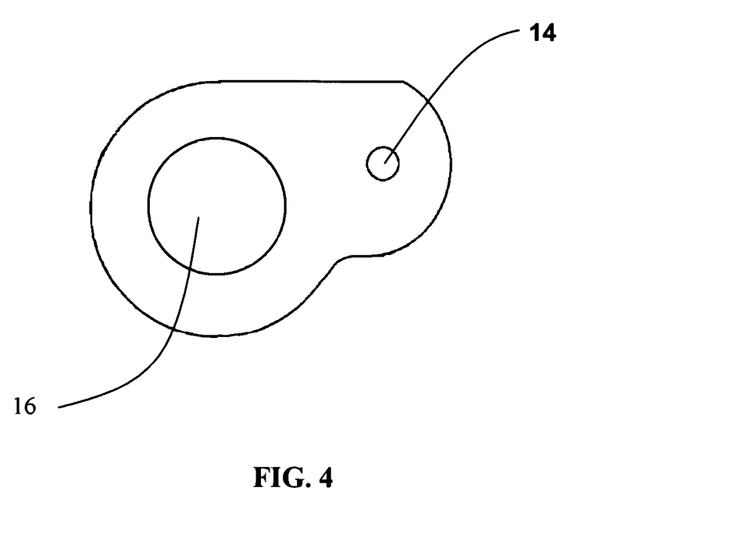
FIG. 4 is a side plan view of the spinous process spacer of FIG. 3.

As depicted in FIGS. 3-6, the main chamber 16 extends through the lateral sides of the spacer 12. The main chamber 16 may be provided in any of a variety of suitable shapes in addition to the generally cylindrical shape as shown by example, including but not limited to generally oblong, triangular, rectangular and/or combinations thereof. As shown in FIG. 3, a pair of apertures 18 dimensioned to receive at least a portion of an insertion tool (not shown) may be located on either the posterior or anterior side of the SPS 10 and extend at least a portion of the way through the body 12. The fusion notch 20 includes a slot or indent dimensioned to receive a portion of the first spinous process 2 (or other vertebral structure) to enhance fusion. The fusion notch 20 may be located generally towards the middle portion of the top of the SPS 10, between the flanges 13. The notch 20 helps position the SPS 10 relative to the first spinous process 2.

Figure 5:
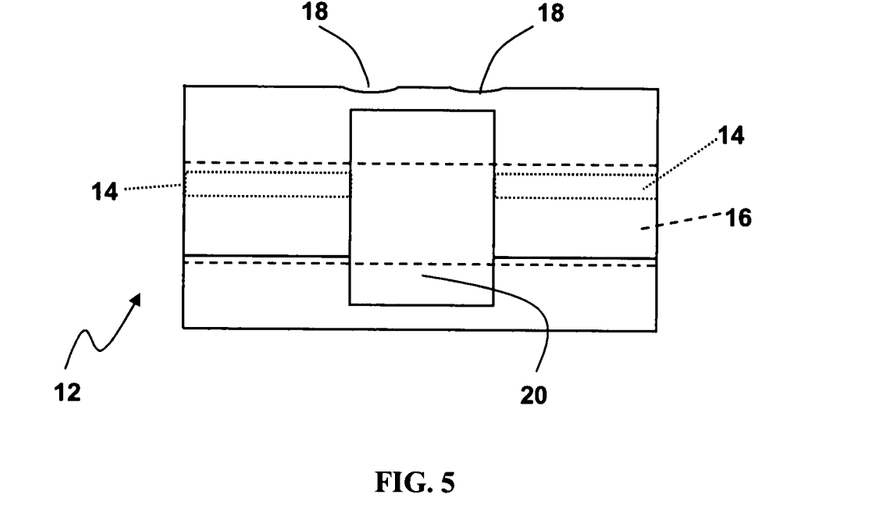
FIG. 5 is a front plan view of the spinous process spacer of FIG. 3.
Figure 6:
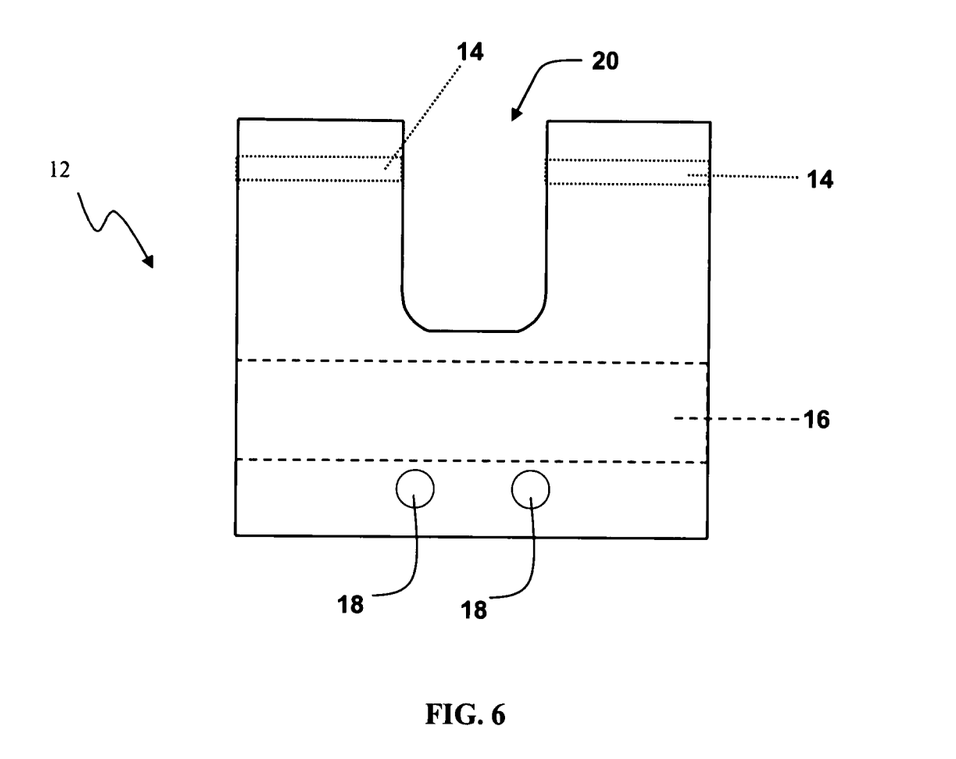
FIG. 6 is a top plan view of the spinous process spacer of FIG. 3.

In FIGS. 5 and 6, the main chamber 16 and apertures 14 are shown by dashed lines, indicating their relative positions within the body 12. FIG. 6 best depicts the U-shape configuration of one embodiment of the SPS 10, shown and described herein by way of example, such that the SPS 10 may accommodate a portion of the first spinous process via the fusion notch 20. This accommodating shape provides stability and increased fusion due to the relatively generous amount of surface area of the SPS 10 in contact with the spinous process. In the example shown in FIG. 6, the SPS 10 is further provided with apertures 18 located on one end of the body 12, the apertures 18 dimensioned to receive at least a portion of an insertion tool. Other insertion tool engagement features may be provided without departing from the scope of the present invention.

Figure 7:
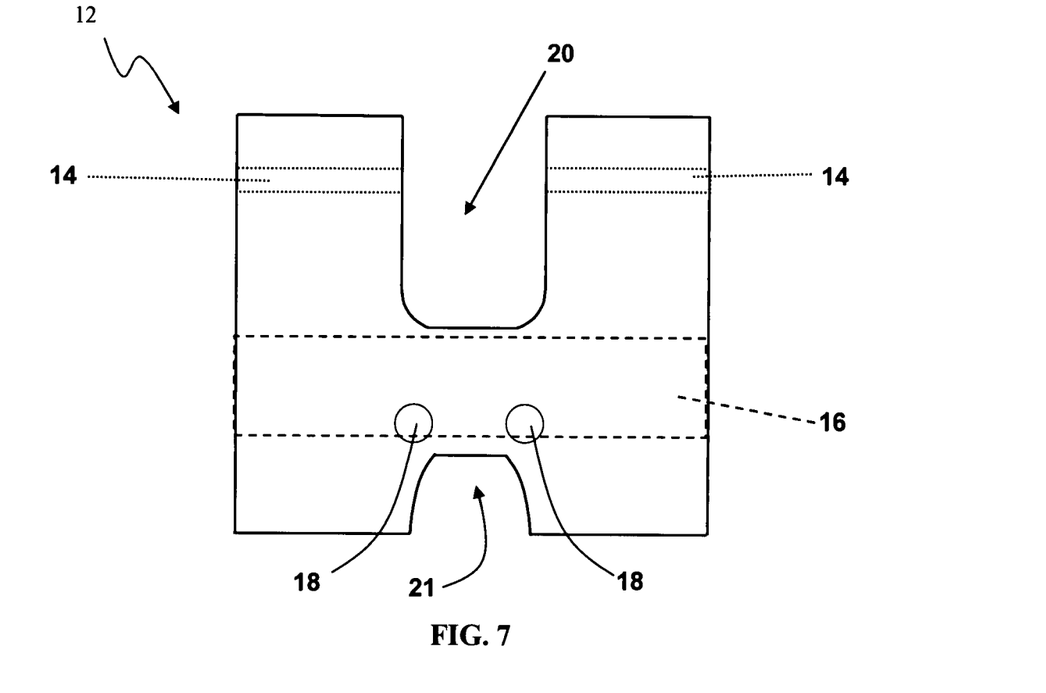
FIG. 7 is a top plan view of a spinous process spacer according to an alternative embodiment of the present invention.
Figure 8:
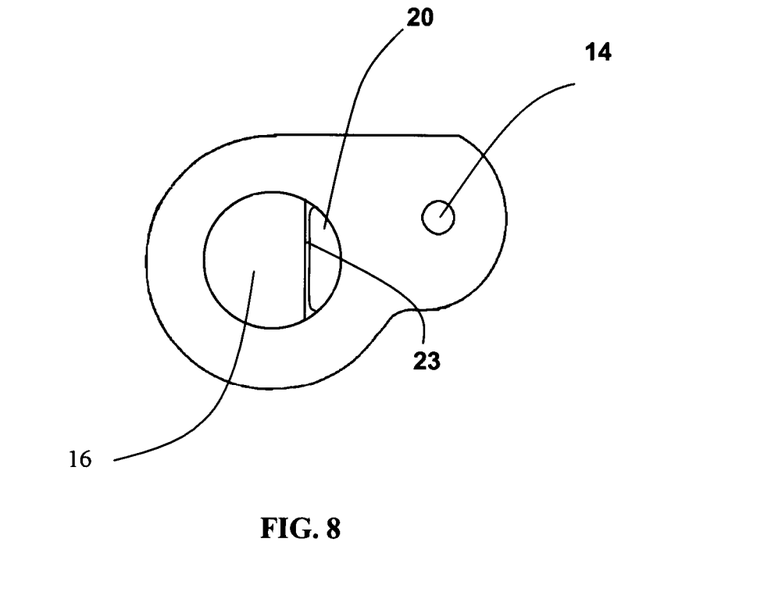
FIG. 8 is a side plan view of the spinous process spacer of FIG. 7.
Figure 9:
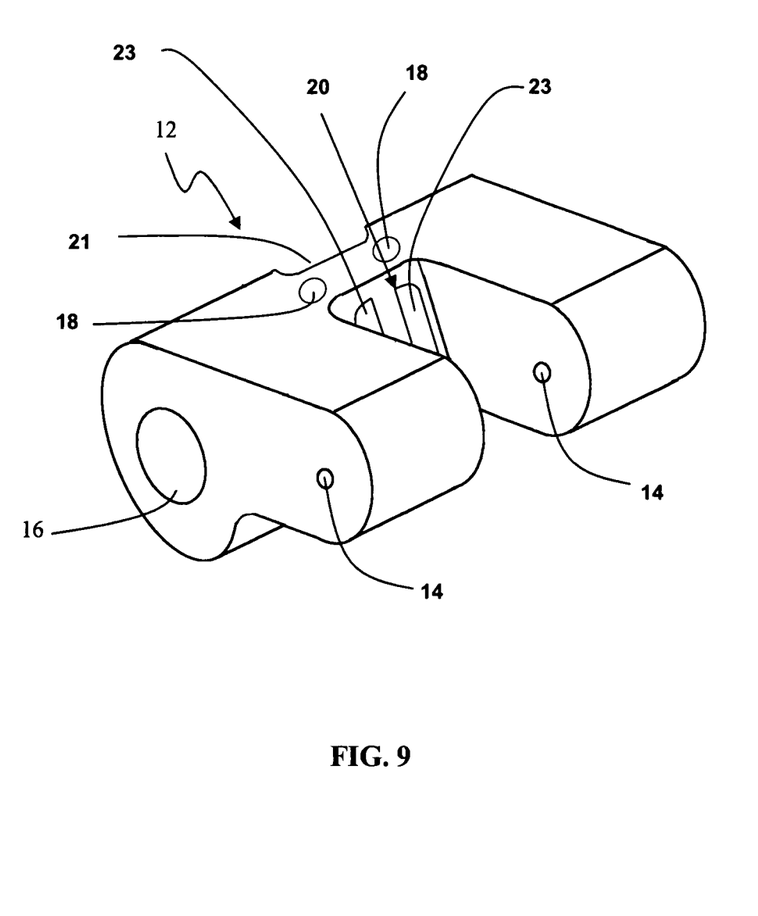
FIG. 9 is a perspective view of the spinous process spacer of FIG. 7.

According to an alternative embodiment of the present invention, shown by way of example in FIGS. 7-9, the body 12 may be provided with a second notch 21 opposite the fusion notch 20, giving the SPS 10 a modified "H" shape. The second notch 21 is dimensioned to receive a second, adjacent spinous process during use, which may assist in maintaining the body 12 in a desired position relative to the adjacent spinous process. Further alternate embodiments of the device could utilize any number of different shapes, including, by way of example only, a wedged or "V" shape.

As shown in FIGS. 8 and 9, the fusion notch 20 may be further provided with slots 23 extending into the main chamber 16. When the SPS 10 is coupled to the first spinous process, these slots 23 will establish direct communication between fusion-inducing compounds provided within the main chamber 16 and the lower aspect of the first spinous process, which advantageously augments the ability of the SPS 10 to fuse to the spinous process (particularly if the SPS 10 is constructed of non-bone materials).

Figure 10:
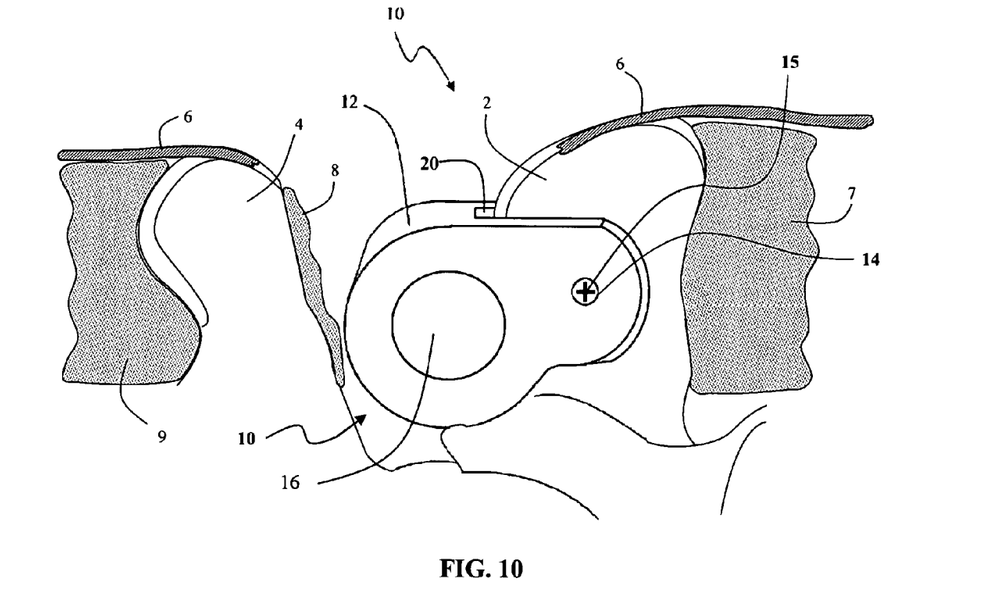
FIG. 10 is a side view of a spinous process spacer implanted between the spinous processes of a pair of adjacent vertebrae, according to one embodiment of the present invention, illustrating the spinous process spacer affixed to one spinous process, and further illustrating the disruption of the supraspinous ligament and the intraspinous ligament during insertion.

During insertion of the SPS 10, it may become necessary to sever the supraspinous and interspinous ligaments. FIG. 10 illustrates an SPS 10 attached to a first spinous process 2 as described above. Supraspinous ligament 6 is illustrated having been severed during the insertion process. Interspinous ligaments 7 and 9 remain intact, while interspinous ligament 8 (situated between first spinous process 2 and second spinous process 4) is also severed.

Figure 11:
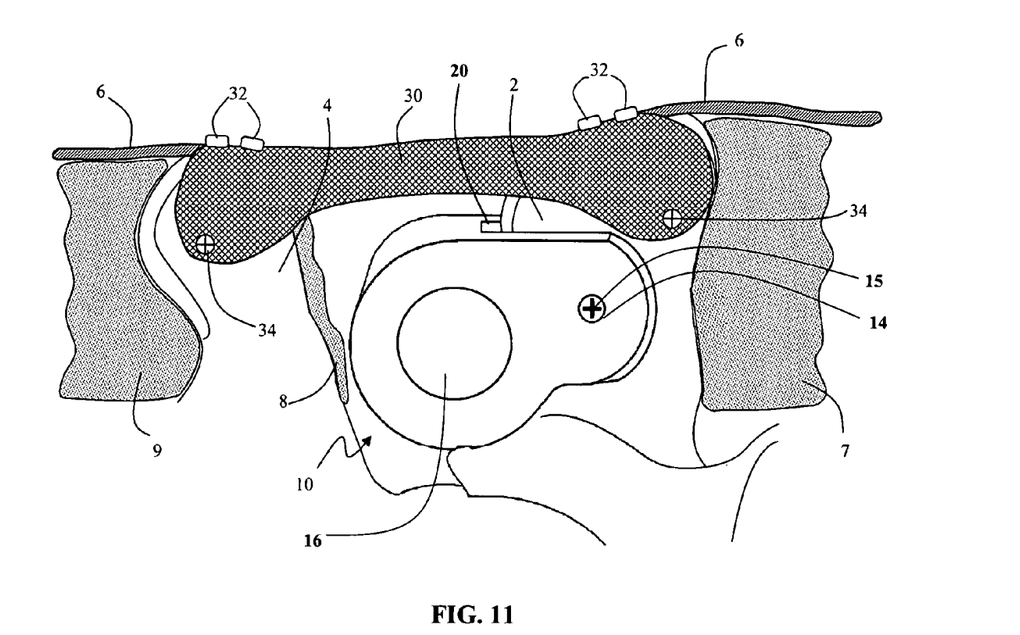
FIG. 11 is a side view of the affixed spinous process spacer of FIG. 10, illustrating the further use of an overlay spanning from one spinous process to the other, primarily covering the posterior portions of the spinous processes.

FIG. 11 illustrates one embodiment of the present invention, in which the SPS 10 may further include an overlay 30 designed to extend between the first and second spinous processes 2, 4 in order to restore the integrity and functional benefits of the supraspinous ligament 6. By way of example only, overlay 30 may be any material suitable for restoring the structural and functional integrity of the supraspinous ligament 6, including but not limited to a surgical mesh or patch manufactured from any suitable biocompatible fiber or textile (such as polyester) via any suitable technique (such as embroidery). Exemplary textiles are shown and described in commonly owned U.S. Pat. No. 5,990,378 entitled "Textile Surgical Implants," and commonly owned U.S. patent application Ser. No. 10/398,883 entitled "Textile Prosthesis," both of which are incorporated by reference herein in their entireties.

As shown in FIG. 11, anchors 32 may be used to secure the overlay 30 to the spinous processes 2, 4. Preferably, anchors 32 are inserted into the posterior portion of the spinous process 2, 4, however it is contemplated that anchors 32 may be inserted into any portion of the spinous process suitable to provide purchase. Optionally, side anchors 34 may be inserted into the side of the spinous processes 2,4 to further secure the overlay 30 to the bone. Anchors 32 and side anchors 34 may be any device suitable for attaching the overlay 30 to the bone, including but not limited to pins, screws, nails, tacks, staples, and the like.

Figure 12:
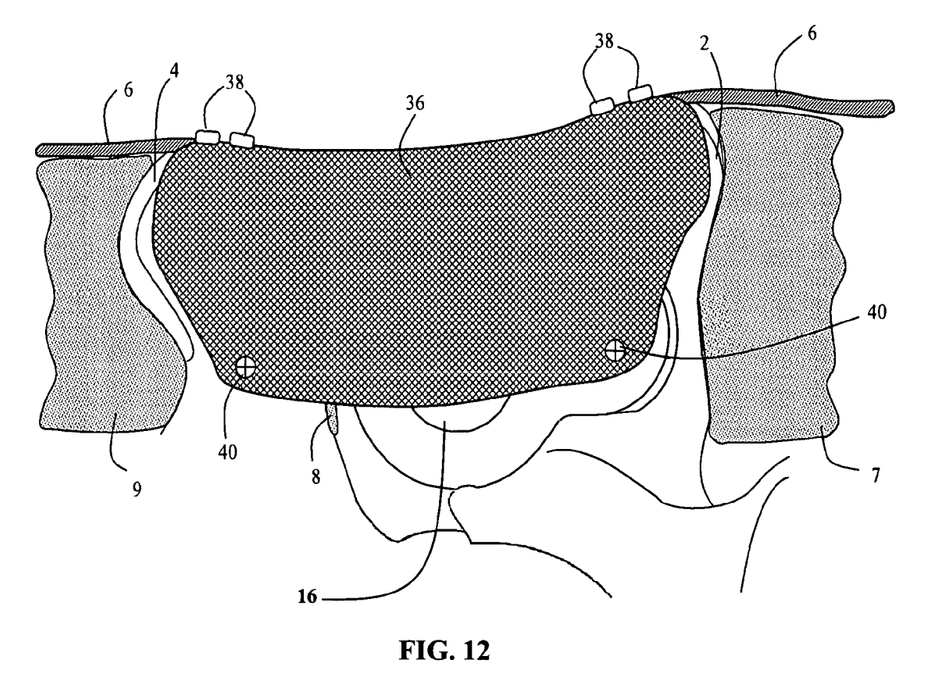
FIG. 12 is a side view of the affixed spinous process spacer of FIG. 10, illustrating the further use of an overlay spanning from one spinous process to the other and covering a larger surface area of the spinous processes.

FIG. 12 illustrates one embodiment of the present invention in which the SPS 10 may further include an overlay 36 designed to extend between the first and second spinous processes 2, 4 in order to restore the integrity and functional benefits of the supraspinous ligament 6 and the interspinous ligament 8. By way of example only, overlay 36 may be any material suitable for restoring the structural and functional integrity of the supraspinous ligament 6, including but not limited to a surgical mesh or patch manufactured from any suitable biocompatible fiber or textile (such as polyester) via any suitable technique (such as embroidery), including the exemplary textiles referenced in the commonly owned patents, above. Anchors 38 may be used to secure the overlay 30 to the spinous processes 2, 4. Preferably, anchors 38 are inserted into the posterior portion of the spinous process 2, 4, however, it is contemplated that anchors 38 may be inserted into any portion of the spinous process suitable to provide purchase. Optionally, side anchors 40 may be inserted into the side of the spinous processes 2, 4 to further secure the overlay 36 to the bone. Anchors 38 and side anchors 40 may be any device suitable for attaching the overlay 36 to the bone, including but not limited to pins, screws, nails, tacks, staples, and the like.

Although shown as separate components, it is contemplated that overlays 30, 36 may be integrally formed with the SPS 10 such that the overlay and spacer are inserted contemporaneously.

The SPS 10 may be dimensioned for use in the cervical and/or lumbar spine without departing from the scope of the present invention. The SPS 10 may be dimensioned, by way of example only, having a length ranging between 6-50 mm and a height ranging between 20-25 mm.

The SPS 10 may be introduced into a spinal target site through the use of any of a variety of suitable instruments having the capability to releasably engage the body 12. In one embodiment, the insertion tool permits quick, direct, accurate placement of the SPS 10 between a first and second spinous process by utilizing the insertion tool apertures 18. An exemplary insertion tool is shown and described in commonly owned U.S. Pat. No. 6,923,814 entitled "System and Method for Cervical Spinal Fusion," which is incorporated by reference herein in its entirety.

In order to use the SPS 10 of the present invention in a treatment of spinal stenosis, a clinician must first designate the appropriate sized body 12. A clinician can utilize the SPS 10 in either an open or minimally invasive spinal fusion procedure. In either type of procedure, a working channel would be created in a patient that reaches a targeted spinal level. After the creation of the working channel, the interspinous space is prepared. The supraspinous and interspinous ligaments may be severed and/or removed. After preparation of the interspinous space, a sizer instrument is used to determine the appropriate size of the body 12. The body 12 is positioned and inserted into the prepared space between the spinous processes. The body 12 may then be mechanically affixed to a spinous process 2, 4 via the fixation element 15. The device forces the spinous processes apart. The spine flexes as the spinous processes are forced apart. The neuroforamina and the spinal canal are enlarged as the spine is flexed, and the implanted SPS 10 holds the vertebrae in a flexed position, in order to relieve the discomfort of spinal stenosis.

Various mechanisms or characteristics may be used to enhance fusion between the implant and the spinous process, including the implant shape, porosity, fixation elements, and the inclusion of bone-growth promoting substances.

When constructed from allograft bone, the SPS 10 may be manufactured according to the following exemplary method. If necessary, first use a belt sander to reduce any high spots or imperfections to standardize the shape of the bone. Cut the allograft bone to length using the band saw. Remove the cancellous material from the inner canal to create the main chamber 16. Using calipers, measure the struts and create a size distribution of SPS 10. Machine the insertion tool apertures 18. Set-up a standard vice for holding the implant across its width on the mill. Use a 3/32" ball end mill to create the apertures 18 (same as cervical allograft implant). Insert the SPS 10 into the vice and tighten. Calculate the centerline of the 20-25 mm long body 12. Create the holes 2.26 mm away from each side of the centerline (4.52 mm hole to hole distance). Create a notch 20 for the spinous process 2, 4. Set-up the cervical allograft holding fixture that uses the apertures 18 and vice to hold the body 12 across its width on the mill. Use a 1/4" flat end mill to create the notch 22. Calculate the centerline of the 20-25 mm long body 12. Insert the body 12 onto the fixture using the apertures 18 and tighten the vice. This automatically verifies the correct sizing/spacing of the apertures 18. Measure the body 12 height. Calculate the cut depth to create the desired body 12 size. Cut the flat on the body 12 to the desired depth. Remeasure the body 12 to insure proper cut depth. Remove the body 12 from the cervical allograft fixture and tighten into the standard vice. Using a battery powered or corded drill with a 1/16" drill bit, drill through the front face to the canal on both sides. Drill the aperture 14 through the face of body 12. Belt sand the face if needed to create a flat surface for the drill bit to engage the body 12.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A system for treating spinal stenosis, comprising:
an implant dimensioned to fit between a first spinous process and a second spinous process, the implant consisting of a body portion and two generally parallel flanges extending generally perpendicularly from the body portion, the body portion including at least one aperture dimensioned to receive at least a portion of an insertion tool, each flange dimensioned to engage a lateral aspect of the first spinous process;
at least one screw configured to affix the implant to the first spinous process; and
an overlay dimensioned to extend from at least a portion of the first spinous process to at least a portion of the second spinous process,
wherein the body portion includes an interior chamber dimensioned to receive fusion inducing material.

2. The system of claim 1, wherein the body portion includes at least one slot in communication with the chamber, the slot configured to allow bone to grow into the implant.

3. The system of claim 2, wherein the body portion further comprises a notch defined between the two flanges and dimensioned to receive a portion of the first spinous process.

4. The system of claim 3, wherein the at least one slot is in communication with the notch.

5. The system of claim 4, wherein the body portion further comprises a second notch dimensioned to receive at least a portion of the second spinous process.

6. The system of claim 2, wherein the fusion inducing material includes any of Bone Morphogenic Protein, demineralized bone matrix, allograft cancellous bone, autograft bone, hydroxyapatite and coral.

7. The system of claim 1, wherein the flanges each include at least one aperture dimensioned to receive the at least one screw.

8. The system of claim 1, wherein the implant is made of a non-bone material.

9. The system of claim 8, wherein the implant is made from one of polyetheretherketone and polyetherketoneketone.

10. The system of claim 1, wherein the overlay comprises at least one of surgical mesh, textile and embroidery.

11. The system of claim 1, further comprising a plurality of anchors to secure the overlay to each of the first spinous process and the second spinous process.

12. The system of claim 11, wherein the plurality of anchors comprise at least one of pins, screws, nails, tacks and staples.

13. The system of claim 1, wherein the overlay is formed as an integral part of the implant.

14. A method for treating spinal stenosis, comprising:
gaining access to an interspinous process space between a first spinous process and a second spinous process;
abrading a portion of the first spinous process;
inserting an implant consisting of a body portion and two generally parallel flanges extending generally perpendicularly from the body portion, the body portion including at least one aperture dimensioned to receive at least a portion of an insertion tool, each flange dimensioned to engage a lateral aspect of the first spinous process, into the interspinous process space;
affixing the implant to the first spinous process with the at least one screw; and
securing an overlay to at least a portion of the first spinous process and at least a portion of the second spinous process such that the overlay extends over the interspinous space.

15. The method of claim 14, wherein the body portion includes at least one slot in communication with the chamber, the slot configured to allow bone to grow into the implant.

16. The method of claim 15, wherein the body portion includes an interior chamber in communication with the at least one slot and comprising the additional step of packing the chamber with fusion inducing material at least one of before and after affixing the implant to the spinous process.

17. The method of claim 16, wherein the fusion inducing material includes at least one of Bone Morphogenic Protein, demineralized bone matrix, allograft cancellous bone, autograft bone, hydroxyapatite and coral.

18. The method of claim 14, wherein the flanges each include at least one aperture dimensioned to receive the at least one screw and comprising the additional steps of:
introducing the at least one screw through the at least one aperture; and
affixing the screw to the first spinous process.

19. The method of claim 14, wherein the body portion further comprises a notch defined between the two flanges and dimensioned to receive a portion of the first spinous process and comprising the additional step of positioning the portion of the first spinous process into the notch during insertion.

20. The method of claim 19, wherein the body portion further includes at least one slot for allowing bone to grow into the implant, the at least one slot being in communication the notch.

21. The method of claim 20, wherein the body portion further comprises a second notch dimensioned to receive at least a portion of the second spinous process.

22. The method of claim 14, wherein the implant is made of a non-bone material.

23. The method of claim 22, wherein the implant is made from one of polyetheretherketone and polyetherketoneketone.

24. The method of claim 14, wherein the overlay comprises at least one of surgical mesh, textile and embroidery.

25. The method of claim 14, wherein securing the overlay comprises introducing at least one anchor into each of the first and second spinous processes and through said overlay.

26. The method of claim 25, wherein the plurality of anchors comprise at least one of pins, screws, nails, tacks and staples.

27. The method of claim 14, wherein the overlay is formed as an integral part of the implant.

28. A system for treating spinal stenosis, comprising:
an implant dimensioned to fit between a first spinous process and a second spinous process, the implant consisting of a body portion and two generally parallel flanges extending generally perpendicularly from the body portion, the body portion including a an interior chamber dimensioned to receive fusion inducing material, at least one slot in communication with the chamber, the slot configured to allow bone to grow into the implant, and a notch defined between the two flanges and dimensioned to receive a portion of the first spinous process, each flange dimensioned to engage a lateral aspect of the first spinous process; and
at least one screw configured to affix the implant to the first spinous process; and
an overlay dimensioned to extend from at least a portion of the first spinous process to at least a portion of the second spinous process.

29. The system of claim 28, wherein the body portion further comprises a second notch dimensioned to receive at least a portion of the second spinous process.

* * * * *